United States Patent [19]

Takaishi et al.

[11] Patent Number: 4,634,719
[45] Date of Patent: Jan. 6, 1987

[54] α-MONO (METHYL-BRANCHED ALKYL) GLYCERYL ETHER AND A SKIN CARE COSMETIC COMPOSITION CONTAINING THE SAME

[75] Inventors: Naotake Takaishi; Kouichi Urata, both of Ichikai; Yoshiaki Inamoto, Utsunomiya; Hisao Tsutsumi, Miyashiro; Junichi Kawano, Sakura, all of Japan

[73] Assignee: Kao Soap Co., Ltd., Tokyo, Japan

[21] Appl. No.: 377,444

[22] Filed: May 12, 1982

Related U.S. Application Data

[63] Continuation of Ser. No. 181,659, Aug. 26, 1980, abandoned.

[30] Foreign Application Priority Data

Sep. 4, 1979 [JP] Japan .................................. 54-113188

[51] Int. Cl.$^4$ ............................................. A61K 47/00
[52] U.S. Cl. .................................. 514/772; 568/680; 514/785
[58] Field of Search ................ 568/680; 424/365, 170, 424/168; 514/772

[56] References Cited

U.S. PATENT DOCUMENTS

| | | | |
|---|---|---|---|
| 3,342,876 | 9/1967 | Chalmers et al. | 568/680 |
| 3,879,346 | 11/1975 | Friedrich et al. | 260/DIG. 15 |
| 4,244,827 | 1/1981 | Michaelis | 568/679 |
| 4,245,125 | 1/1981 | Wirth et al. | 568/680 |

FOREIGN PATENT DOCUMENTS

| | | | |
|---|---|---|---|
| 49-92239 | 9/1974 | Japan . | |
| 52-12109 | 1/1977 | Japan . | |
| 1539625 | 1/1979 | United Kingdom | 568/679 |

Primary Examiner—Howard T. Mars
Attorney, Agent, or Firm—Oblon, Fisher, Spivak, McClelland & Maier

[57] ABSTRACT

α-mono(methyl-branched alkyl) glyceryl ethers represented by the formula

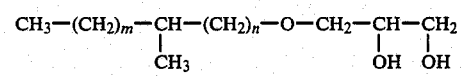

where m is an integer of 2 to 14, n is an integer of 3 to 11, and the total of m+n is 11 to 17, are disclosed along with skin care compositions containing the same as emulsifiers.

2 Claims, No Drawings

α-MONO (METHYL-BRANCHED ALKYL) GLYCERYL ETHER AND A SKIN CARE COSMETIC COMPOSITION CONTAINING THE SAME

This is a continuation of application Ser. No. 181,659, filed Aug. 26, 1980, now abandoned.

BACKGROUND OF THE INVENTION

1. Field of the Invention

The present invention relates to a novel α-monoalkyl glyceryl ether and a cosmetic composition containing it.

2. Description of the Prior Art

As α-monoalkyl glyceryl ether, there have been known palmityl glyceryl ether (also called "chimyl alcohol"), stearyl glyceryl ether (also called "batyl alcohol") and oleyl glyceryl ether (also called "selachyl alcohol") which are present in the lipid of fish. It is known that they have excellent properties as an emulsifier, particularly as a W/O type emulsion stabilizer and further that they have medicinal activities such as an acceleration effect for the blood cell formation in the marrow, an anti-inflammatory affect and an antitumor activity.

However, these known α-monoalkyl glyceryl ethers have certain drawbacks such that they are solids having high melting points, their lipophilic property is too high, those having unsaturated bonds are chemically unstable and some of them are irritant to the skin.

There have been some proposals to remove these drawbacks. For instance, there has been proposed a α-monoalkyl glyceryl ether wherein a long chain alkyl group having a substituent group constituting a straight chain or a branched chain at β-position, is used as the alkyl group (Japanese laid-open patent application No. 12109 of 1977).

A need continues to exist for an emulsifier for cosmetic compositions which is liquid at room temperature, is chemically stable, has good emulsion stabilisation effect and gives no irritation to the skin.

SUMMARY OF THE INVENTION

Accordingly, one object of the invention is to provide an emulsifier which is liquid at room temperature, is chemically stable, has good emulsion stabilization effect and gives no irritation to the skin.

A further object of the invention is to provide a cosmetic composition containing such an emulsifier.

Briefly, these objects and other objects of the invention, as hereinafter will become more readily apparent, can be attained by providing an α-mono(methyl-branched alkyl)glyceryl ether represented by the formula (I):

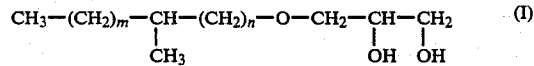

where: m is an integer of 2 to 14; n is an integer of 3 to 11; and the total of m+n is 11 to 17.

DETAILED DESCRIPTION OF THE PREFERRED EMBODIMENTS

The novel α-mono(methyl-branched alkyl)glyceryl ether of the present invention, represented by the formula (I), can be prepared from the corresponding alchol (II)

ROH     (II)

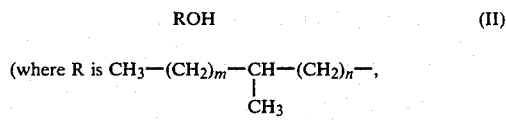

and m and n are as defined above) by known processes.

The alcohol (II) may be reacted with a halogenation agent to obtain the corresponding alkyl halide (II), and this alkyl halide is then reacted with a glycerol alkali metal alcoholate having protected hydroxyl groups at 2 and 3 positions to obtain a 1-alkyl glyceryl ether (IV) having protected hydroxyl groups at 2 and 3 positions, which is then subjected to hydrolysis. The reactions are represented by the following formulas:

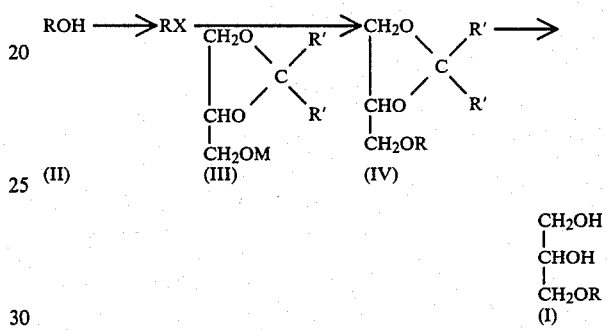

(where R' is a lower alkyl group or a phenyl group, M is an alkali metal and R is as defined above).

The alkyl halide (II) may be prepared from the alcohol (II) by a conventional process of converting an alcoholic hydroxyl group into an halogen. For instance, halogenation agents well-known in the art such as chlorination agents e.g. thionyl chloride, phosphorus trichloride and phosphorus pentachloride; bromination agents e.g. phosphorus tribromide, phosphorus pentabromide, and mineral acid/aqueous hydrobromide; and iodination agents e.g. red phosphorus/iodine, may be used in ordinary conditions to obtain the alkyl halide (III) in good yield.

Then, the alkyl halide is reacted with a glycerol alkali metal alcoholate having hydroxyl groups at the 2 and 3 positions protected with proper protecting groups, to produce a 1-alkyl glyceryl ether (IV). In order to protect the hydroxyl groups, ketones are suitably used, and acetone is particularly preferred. As an alkali metal for the alcoholate, sodium or potassium is suitable, and the alcoholate may be prepared by reacting the corresponding glycerol with an alkali metal or its hydroxide. The ether (IV) may be prepared from the alkyl halide (III) and the alcoholate in the reaction conditions normally used in a usual etherification process. No catalyst is normally required, and the reaction will be completed simply by heating the reactants in a suitable solvent. About 1 to 5 moles, preferrably about 2 to 3 moles of the alcoholate per mole of the alkyl halide (III) are used, and the reaction, if conducted at a temperature of 120° to 160° C., preferably 140° to 160° C., will be completed in a few hours. According to the most preferred embodiment, about 3 moles of a sodium alcoholate of isopropylidene glycerol per mole of an alkyl chloride (III, X is Cl) are refluxed in xylene as a solvent for a few hours under heating.

The desired alkyl glyceryl ether (I) is prepared by hydrolysing the 1-alkyl glyceryl ether having protected hydroxyl groups at the 2 and 3 positions (IV) with use of a mineral acid as a catalyst to remove the protecting groups. As the mineral acid, sulfuric acid, hydrochloric acid, nitric acid or phosphoric acid may be used. However, the most practical one is sulfuric acid. It is preferred that 0.5 to 3.0N, preferable 1.0 to 2.0N of the mineral acid be used. The hydrolysis can suitably be conducted at 50° to 100° C., and it is most advantageous to add a lower alcohol such as methanol or ethanol and to reflux at its boiling point.

Further, α-mono(methyl-branched alkyl)glyceryl ether (I) of the present invention may alternatively be prepared by reacting an alcohol (II) with an epihalohydrin to produce an alkylhalohydrin ether (V), which is then ring closed to give an alkyl glycidyl ether (VI), which is in turn subjected to hydrolysis. These reactions are represented by the following formulas:

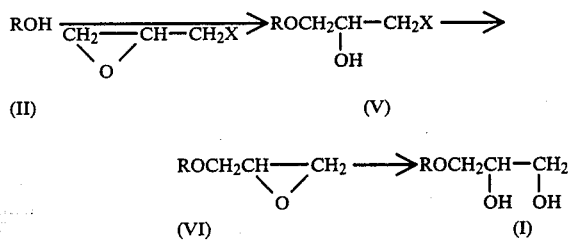

(where X is a halogen atom and R is as defined above).

The reaction of the alcohol (II) and the epihalohydrin is most suitably carried out in the presence of a mineral acid, or a Lewis acid or base, as catalyst, with use of 1 to 5 moles of the alcohol per mole of the epihalohydrin at a temperature of about 80° to 120° C. As the epihalohydrin, epichlorohyrin or epibromohydrin is preferably used. The ring closure glycidylation reaction of the alkylhalohydrin ether (V) is carried out with the reaction conditions normally used in the ring closure reaction of a halohydrin. Namely, the glycidyl ether (VI) is obtained by adding an alkali catalyst to the halohydrin (V) and heating it. The halohydrin (V) obtained in the preceding step may be subjected to the ring closure reaction without isolation. In such as case, it is preferred to heat at about 50° to 150° C. in the presence of about 1 to 5 moles of an alkali per mole of the epihalohydrin used. As the alkali, alkali metal hydroxides such as sodium hydroxide, and potassium hydroxide, and alkali metal carbonates such as sodium carbonate, are preferred.

The desired α-mono(methyl-branched alkyl)glyceryl ether (I) is obtained by ring opening the alkyl glycidyl ether (VI) in the conditions used for a normal ring opening reaction of an epoxide. The ring is most commonly opened by means of hydrolysis in the presence of an acid catalyst, and it is preferred to heat with an aqueous solution of a mineral acid such as sulfuric acid, hydrochloric acid, nitric acid or phosphoric acid. The mineral acid is preferably of a concentration of 0.1 to 5N. The reaction will be completed by heating at a temperature of 80° to 150° C. for a few hours with use of an ether solvent such as diethylene glycol dimethyl ether or an alcohol solvent, and the catalyst.

The alcohol (II) to be used as the starting material in the present invention may be prepared by reducing the corresponding carboxylic acid ester, for example by a high pressure catalytic reduction with use of a hydrogenation catalyst, e.g., a copper-chromium catalyst. As the corresponding carboxylic acid, there may be mentioned, for example, an acid which is obtained as a by-product in the production of oleic acid dimer and which contains, as principal component, iso-stearic acid having methyl branches and having about 18 carbon atoms.

The α-mono(methyl-branched alkyl)glyceryl ether represented by the formula (I) of the present invention preferably has the total of m and n in the formula (I) of 13 to 17 (namely, a total carbon number in the alkyl group is 16 to 20) and more preferably has the total of m and n of 15 (namely, a total carbon number in the alkyl group is 18). Further, it is preferred that the branched methyl group is located in the vicinity of the center of the main alkyl chain. An industrially produced alcohol (II) is a mixture having a certain distribution of total carbon numbers in the alkyl groups and the location of the branched methyl groups. For instance, the above-mentioned iso-stearyl alcohol which is obtained as a by-product in the production of oleic acid dimer and which is a reduction product of isostearic acid having methyl branches, contains about 75% or more of the one having a total carbon number of 18 (i.e. a total of m and n being 15) and the rest being composed of those having a total carbon number of 14, 16 or 20, and the branched methyl groups are located at the central portion of the main alkyl chain (J. Amer. Oil Chem. Soc. 51, 522 (1974).

The α-mono(methyl-branched alkyl)glyceryl ether of the present invention is liquid at a room temperature; contains no double bond or ester bond, thus it is chemically stable; superior in the emulsifying power; and gives no irritation to the skin. Thus, it is extremely useful as an emulsifier for a skin care cosmetic composition.

The characteristics of the representative compound of the α-mono(methyl-branched alkyl)glyceryl ether of the present invention are as follows:

| Methyl-branched alkyl group | Melting point | Specific gravity (30° C.) | Viscosity (30° C.) |
|---|---|---|---|
| Methyl-branched stearyl (principal component, m = 7, n = 8) | 23° C. | 0.912 | 856 |

With use of the α-mono(methyl-branched alkyl)glyceryl ether of the present invention as an emulsifier for a skin care composition, it is possible to readily obtain an emulsion type cosmetic composition such as a milky lotion or a cream which has a good texture, luster, emulsion stability, and no irritation to the skin, and which gives a good feeling upon application to the skin.

The skin care cosmetic preparations are used to protect the skin from drying or irritation or to prevent the skin from roughening or to maintain skin freshness. Such cosmetic compositions may take the form of a vanishing cream, a cold cream, a milky lotion or a cosmetic lotion.

The components of an emulsion type cosmetic composition include water and an oil in addition to the α-mono(methyl-branched alkyl)glyceryl ether as the emulsifier. As such an oil, there may be mentioned a hydrocarbon such as liquid paraffin, vaseline, paraffin wax, squalane, or ceresine wax; an ester such as bees wax, whale wax, carnauba wax, hydrous lanolin, or an ester synthesized from a higher alcohol and an aliphatic acid; a plant oil such as olive oil, camellia oil, cotton oil, or jojoba oil, an alcohol such as a long chain aliphatic alcohol, or hydrous lanolin alcohol; and an aliphatic acid such as a stearic acid. The emulsion type cosmetic composition may contain about 0.1 to 30% by weight of the α-mono(methyl-branched alkyl)glyceryl ether, 1 to 98.9% by weight of water and 1 to 60% by weight of the oil.

A portion of the α-mono(methyl-branched alkyl)-glyceryl ether as the emulsifier may be substituted by an emulsifier employed as an emulsifier for conventional cosmetic compositions. As such an emulsifier, there may be mentioned, for example, a polyoxyethylene alkyl ether, a polyoxyethylene sorbitan fatty ester, a polyoxyethylene fatty acid ester, a polyoxyethylene hardened castor oil, a polyoxyethylene sorbitol fatty acid ester, a sucrose fatty acid ester, a sorbitan fatty acid ester, glyceryl fatty acid ester, saponified fatty acid, an alkyl sulfuric acid ester, an alkyl phosphoric acid ester, or polyoxyethylene alkyl phosphoric acid ester.

Further, the skin care cosmetic composition of the present invention may contain other components which are usually employed to improve the quality of the cosmetic compositions, if desired. Such other components include a moisturizer such as glycerin, sorbitol, propylene glycol, 1,3-butylene glycol; a perfume; a thickening agent; a medicinal agent; and an antiseptic agent.

Having generally described this invention, a further understanding can be obtained by reference to certain specific examples which are provided for purposes of illustration only and are not intended to be limiting unless otherwise specified.

PREPARATORY EXAMPLE (Preparation of the Alcohol of the Formula (II))

4770 g of isostearic acid isopropyl ester (Emery 2310 isostearic acid isopropyl ester, sold by Emery Industry Inc., U.S.A.) and 239 g of a copper-chromium catalyst (made by Nikki) are charged in an autoclave having a capacity of 20 liters. Hydrogen gas is then added under a pressure of 150 kg/cm$^2$ and the reaction mixture is heated to a temperature of 275° C. Hydrogenation was carried out under a pressure of 150 kg/cm$^2$ at 275° C. for about 7 hours, and then the reaction product was cooled and the catalyst residue was removed by filtration, whereupon 3500 g of a crude product were obtained. The crude product was distilled under reduced pressure thereby obtaining 3300 g of a colourless transparent isostearyl alcohol as a distillate at 80° to 167° C./0.6 mmHg. The isostearyl alcohol (methyl-branched stearyl alcohol) thus prepared had an acid value of 0.05, a saponification value of 5.5, and a hydroxyl value of 181.4. Absorption was observed at 3340 and 1055 cm$^{-1}$ by IR (liquid film) and at δ3.50 (broad triplet, —C$\underline{H}$H$_2$—OH) by NMR(CCl$_4$). It has been found from gas-chromatography that the alcohol consists of a mixture which comprises about 75% of the main component having a total carbon number of 18 (the total of m and n being 15 in the formula II) and the rest being composed of components having a total carbon number of 14 or 16, and that, in any case, branched methyl groups are located in the vicinity of the center of the main alkyl chain.

EXAMPLE 1

(i) Into a reactor having a capacity of 5 liters and equipped with a thermometer, a reflux condenser, a dropping funnel, a nitrogen gas supply line, and a stirrer, 2444 g of the isostearyl alcohol obtained by the Preparatory Example was introduced. While stirring and supplying a nitrogen gas, thionyl chloride was added dropwise from the dropping funnel. Heat and gas were generated from the reaction mixture. The temperature of the reaction mixture rose to 31° C. at the initial stage of the reaction, but gradually dropped down to about 18° C. as the amount of the added thionyl chloride increased. Then, the reaction mixture was heated to about 40° C. and thionyl chloride was continuously added dropwise. When the generation of the gas weakened, the reaction mixture was heated to 70° to 80° C., whereupon the generation of the gas started again vigorously, and thionyl chloride was further added dropwise. When the generation of the gas completely ceased, the dropping of thionyl chloride was stopped. The total amount of thionyl chloride added was 2200 g. The reaction product was cooled and was further stirred at 70° to 80° C. for about 1 hour.

The reaction mixture was cooled, a low boiling point distillate (composed mainly of unreacted thionyl chloride) was removed under atmospheric pressure at 40° to 50° C., and the residue was cooled by ice and, while stirring, ice cubes were added little by little. After ascertaining that the vigorous gas generation was stopped, ether was added and then water was added, and the mixture was thoroughly stirred. The ether layer was separated, neutralized with sodium bicarbonate, and after removal of the solvent, distilled under reduced pressure to obtain 2217 g of isostearyl chloride (X is Cl in the formula III) from the distillate at 103° to 163° C./0.1 to 1.0 mm Hg.

IR (liquid film): 725 and 650 cm$^{-1}$

NMR (CCl$_4$): δ3.50 (triplet, —CH$_2$Cl)

(ii) 798 g of isopropylidene glycerol, 1500 ml of xylene, 340 g of a 93% sodium hydroxide and 300 g of water were charged in a reactor having a capacity of 5 liters and equipped with a thermometer, a stirrer, a dropping funnel and Dean-Stark trap, and while stirring, refluxed at 130° to 140° C. Water was separated in the Dean-Stark trap from the distilled water/xylene mixture, and discarded out of the reaction system, and the xylene was returned to the reaction system. After refluxing for about 16 hours, when distillation of water is no longer observed, 777 g of the isostearyl chloride prepared in step (i) was added dropwise from the dropping funnel in about 30 minutes. After the completion of the dropping, the reaction mixture was further refluxed for about 9 hours at 130° to 140° C. to complete the reaction. After cooling, sodium chloride precipitate at the bottom of the reactor was removed by filtration, the solvent was removed under reduced pressure, and 800 g of a distillate at 176° to 206° C./0.25 to 0.50 mmHg was collected. This was 2,3-O-isopropylidene-1-O-isostearyl glyceryl ether (R' is CH$_3$ in the formula IV).

IR (liquid film): cm$^{-1}$; 1200 to 1260, 1050 to 1120 (C-O stretching vibration).

NMR (CCl$_4$): δ; 3.1 to 4.2

(multiplet, —CH₂—O—CH₂CH——CH₂)
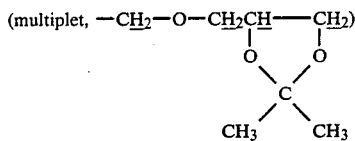

(iii) 1103 g of the isopropylidene iso-stearyl glyceryl ether obtained in step (ii) were charged in a reactor having a capacity of 5 liters and equipped with a stirrer, a thermometer, and a reflux condenser, and then 1500 ml of ethanol and 2000 ml of a 0.1N sulfuric acid were added thereto. While stirring, the mixture was refluxed at 80° to 85° C. After about 10 hours, it was ascertained by gas chromatography that the hydrolysis of the isopropylidene isostearyl glyceryl ether was completed.

The reaction mixture was left to cool and an oil layer and a water layer were separated from each other. The water layer was extracted with ether, and the extracts were added to the oil layer, and an aqueous solution of sodium bicarbonate was added to neutralize the remaining acid. After the separation of the organic layer, the solvent was removed under reduced pressure and dried at 100° under 0.1 mmHg for 3 hours. 900 g of α-mono(isostearyl)glyceryl ether were obtained as a colourless transparent liquid.

IR (liquid film): 3400, 1050 to 1140 cm⁻¹.
NMR (CCl₄): δ; 3.2 to 3.8

(multiplet, —CH₂—O—CH₂—CH—CH₂)
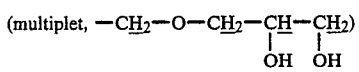
                                    OH  OH Acid value: 0.08; saponification value: 0.36.
Hydroxyl value: 313.8; Iodine value: 0.32.

EXAMPLE 2

(i) 250 g (0.93 mole) of the isostearyl alcohol obtained in the Preparatory Example were charged in a reactor having a capacity of 3 liters and equipped with a thermometer, a reflux condenser, a dropping funnel and a stirring, and while stirring, 2 ml of a boron trifluoride diethyl ether complex were added at room temperature. The mixture was heated to 85° C. and 150 g (1.63 mole) of epichlorohydrin were added dropwise from the dropping funnel over about 2 hours. As the reaction was exothermic, the reaction temperature was controlled by cooling so that the temperature of the mixture fell within the range of 100° to 110° C. After the completion of the dropping, the stirring was continued for a further 3 hours at 100° C. It ascertained by gas chromatography that the compositional ratio of unreacted alcohol and isostearyl chlorohydrin ether (X is Cl in the formula V) was about 1:3.

(ii) While stirring and without isolating the isostearyl chlorohydrin ether, the reaction mixture of step (i) was dropwisely added with 400 g of an aqueous solution of 40% sodium hydroxide from the dropping funnel and then 400 g of tertiary butyl alcohol were added dropwise. After the termination of the dropping, heat refluxing was continued at 80° C. for a further 2 hours while stirring. At the same time as the commencement of the refluxing, sodium chloride started to precipitate, the rate of the precipitation increased as time passed. After ascertaining by gas chromatography that the chlorohydrin ether had completely disappeared the reaction was stopped. The precipitated sodium chloride was removed by filtration, and the filtrate was left to stand whereupon an oil layer and a water layer were separated. The oil layer was distilled under reduced pressure to remove the solvent, and 50 g of unreacted alcohol and then 170 g of isostearyl glycidyl ether (formula VI) as a distillate at 160° to 170° C./0.4 mmHg were obtained.

IR (liquid film): cm⁻¹; 1240, 1100, 920, 845.
NMR (CCl₄): δ; 2.3 to 3.7

(multiplet, —CH₂—O—CH₂—CH——CH₂)
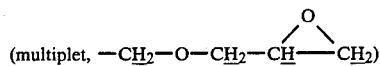

(iii) 140 g of the isostearyl glycidyl ether obtained in step (ii) and 400 ml of diethylene glycol dimethyl ether were introduced into a reactor having a capacity of 3 liters and equipped with a stirrer, a thermometer, a reflux condenser and a dropping funnel. While stirring the mixture, 800 ml of a 0.5N sulfuric acid were added dropwise from the dropping funnel. After the termination of the dropping, the mixture was heated to 100° to 110° C. and stirred for about 8 hours at this temperature. By gas chromatography, it was ascertained that the glycidyl ether had completely disappeared. The reaction product was cooled and left to stand whereupon an oil layer and a water layer were separated. The water layer was extracted with ether, and the extracts were combined with the oil layer and sodium bicarbonate was added to neutralize the remaining acid. The oil layer was separated, the solvent was removed under reduced pressure, and dried at 100° C. under 0.1 mmHg. for 3 hours. 120 g of a colourless transparent liquid were obtained. The gas chromatograph, IR and NMR of this liquid were the same as those obtained with the α-mono(isostearyl)glyceryl ether obtained in Example 1.

EXAMPLE 3

Emulsification tests were conducted with use of the compound of the present invention prepared in Example 1 and comparative products to compare the emulsifying effectiveness. The emulsification tests were carried out with use of liquid paraffin as the oil under the following conditions: 3 weight parts of a compound to be tested were mixed with 20 weight parts of liquid paraffin, and the mixture was heated to 70° C. To this mixture of liquid paraffin and the compound to be tested, 77 weight parts of an ion-exchanged water which was likewise heated at 70° C. was added while stirring, thereby emulsifying the mixture. After the emulsification, the mixture was cooled, while stirring, down to room temperature.

The emulsification powers were evaluated by observing the state of separation immediately after the formation of the emulsion, and 7 days after keeping it at a temperature of 25° C. The results are shown in Table 1.

TABLE 1

| Compounds tested | Immediately after formation | Separation* rate after 7 days |
|---|---|---|
| Present Invention | | |
| α-mono (isostearyl) glycerly ether | Homogeneous W/O cream | 0 |
| Comparative Products | | |
| α-mono (stearyl) glyceryl ether (Batyl Alcohol) | Slightly non-homogenous W/O cream | 14 |
| α-mono (oleyl) | Homogeneous | 7 |

TABLE 1-continued

| Compounds tested | Immediately after formation | Separation* rate after 7 days |
|---|---|---|
| glyceryl ether (Selachyl Alcohol) | W/O cream | |
| α-mono(2-Hexadecyleicosyl) glyceryl ether | Separation into oil and water | 100 |
| α-mono(2-dodecyloctadecyl) glyceryl ether | Separation into oil and water | 100 |

*Separation Rate (%) =

$$\left( \frac{\text{Separated oil phase (ml)} + \text{Separated water phase (ml)}}{\text{Whole volume (ml)}} \right) \times 100$$

TABLE 2

| Compounds tested | Irritation to the skin | Other skin Changes |
|---|---|---|
| Present Invention | | |
| α-Mono(isostearyl) glyceryl ether | (±) | Same as water |
| Comparative Products | | |
| α-Mono-oleyl gyceryl ether (selachyl alcohol) | (+) | Scale failing observed |
| Oleic acid monoglyceride | (++) | Strong skin response |
| Stearic acid monoglyceride | (+) | Slight luster |
| Sorbitan mono-oleate | (±) | Slight luster |
| Water | (−) | No change |

TABLE 3

| Compounds tested | Sticky feeling | Texture | Luster | Stretchability | Hardness |
|---|---|---|---|---|---|
| Present Invention | | | | | |
| α-Mono(isostearyl) glyceryl ether | −0.9 | +1.7 | +1.6 | +0.3 | −0.2 |
| Comparative Products | | | | | |
| α-Mono-oleyl glyceryl ether (Selachyl alcohol) | +1.1 | +0.2 | +0.1 | +0.2 | −1.4 |
| Oleic acid monoglyceride | +1.8 | −0.2 | −0.1 | +0.1 | −0.2 |
| Sorbitan mono-oleate | +0.1 | −1.2 | −1.3 | +0.2 | +0.2 |
| Sorbitan sesqui-oleate | +0.9 | −1.1 | −0.9 | −0.1 | −0.1 |
| Stearic acid monoglyceride | −1.1 | −2.0 | −1.8 | −1.2 | −1.1 |

The numbers in the Table indicate average values by 10 specialist

As is apparent from the above results, the compound of the present invention has an outstanding emulsifying power and has been shown to have even superior emulsion stability to the known batyl alcohol or selachyl alcohol which have been regarded as having a strong emulsifying power. Additionally, the glyceryl ether having an alkyl group having a branched chain at the β-position was dissolved in the oil phase and exhibited no substantial emulsifying power.

EXAMPLE 4

Creams having the following composition and which contain α-mono(isostearyl)glyceryl ether of the invention and comparative compounds, were prepared and tested for irritation to the skin and feeling upon application.

Irritation to the skin was evaluated by open patch tests by applying the respective creams to guinea pigs (3 groups each consisting of 6 guinea pigs) for 4 days and observing the reaction strength of the skin after 5 days. The evaluation was made on the basis of no response (−), a red rash (+) and an edema (++).

The feeling tests were conducted by a panel of 10 specialists and the feeling was evaluated on the basis of the following standards: (+2): Strong, (+1): Moderate, (0): Ordinary, (−1): Slightly bad. The results are shown in Tables 2 and 3. The composition of the creams:

| Compound tested | 4 (%) |
|---|---|
| Liquid paraffin | 10 |
| Bees wax | 3 |
| Cetanol | 2 |
| Polyoxyethylenesorbitan monostearate | 3 |
| Methyl para hydroxy bengoate | 0.1 |
| Butyl para hydroxy bengoate | 0.1 |
| Purified water | the rest |

From the results of the above tests, it is apparent that the cream of the present invention containing α-mono(methyl-branched alkyl)glyceryl ether is less irritant, and superior in the feeling upon application, and has better texture and luster than the creams containing conventional emulsifiers.

EXAMPLE 5

Hand Cream

| | |
|---|---|
| 1. α-Mono (isostearyl glyceryl ether | 2.5 (%) |
| 2. Polyoxyethylene stearate | 1.5 |
| 3. Stearic acid | 10.0 |
| 4. Squalane | 2.0 |
| 5. Cetanol | 1.5 |
| 6. Triethanolamine | 0.5 |
| 7. Antiseptic 0.2 | |
| 8. Sorbitol | 5.0 |
| 9. Perfume | 0.1 |
| 10. Purified water | the rest |

Components 1 to 8 and 10 were mixed and heated to 70° C. After cooling, Component 9 was added to obtain a final product.

EXAMPLE 6

Cleansing Cream

| | |
|---|---|
| 1. Mono(isostearyl) glyceryl ether | 1.8 (%) |
| 2. Polyoxyethylene hardened castor oil | 2.2 |
| 3. Hexadecyle-2-ethyl hexanoate | 20.0 |
| 4. Whale wax | 2.5 |
| 5. Cetanol | 2.0 |
| 6. Liquid paraffin | 18.5 |
| 7. Antiseptic | 0.2 |
| 8. Perfume | 0.1 |
| 9. Purified water | the rest |

The cream was prepared in the same manner as in Example 5.

EXAMPLE 7

Cold Cream (W/O type)

| | |
|---|---|
| 1. α-Mono(isostearyl) glyceryl ether | 2.0 (%) |
| 2. Liquid paraffin | 15.0 |
| 3. Hydrous lanolin alcohol | 1.0 |
| 4. Paraffin wax | 1.0 |
| 5. Antiseptic | 0.1 |
| 6. Propylene glycol | 2.5 |
| 7. Purified water | the rest |

The cream was prepared in the same manner as in Example 5.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A skin care cosmetic composition selected from the group consisting of vanishing cream, cold cream, hand cream, cleansing cream, milky lotion and cosmetic lotion, comprising water, oil and as an emulsifier of oil and water about 0.1% by weight to about 30% by weight of a α-mono(methyl-branched alkyl)glyceryl ether represented by the formula

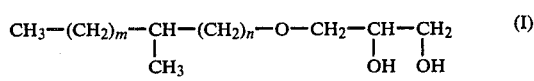

where m is an integer of 2 to 14, n is an integer of 3 to 11, and the total of m+n is 11 to 17.

2. The skin care cosmetic composition according to claim 1, wherein said water is present in an amount of 1 to 98.9% by weight and said oil is present in an amount of 1 to 60% by weight.